United States Patent
Heijmans et al.

(10) Patent No.: US 6,251,887 B1
(45) Date of Patent: Jun. 26, 2001

(54) 17β-ARYL(ARYLMETHYL)OXY(THIO)ALKYL-ANDROSTANE DERIVATIVES

(75) Inventors: Christian Heijmans, Breda; Jaap van der Louw, Oss, both of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/581,749

(22) PCT Filed: Dec. 11, 1998

(86) PCT No.: PCT/EP98/08130
§ 371 Date: Jun. 16, 2000
§ 102(e) Date: Jun. 16, 2000

(87) PCT Pub. No.: WO99/32506
PCT Pub. Date: Jul. 1, 1999

(30) Foreign Application Priority Data

Dec. 18, 1997  (EP) .................................................. 97203998

(51) Int. Cl.[7] .................................. C07J 7/00; C07J 9/00; C07J 51/00; C07J 31/575; C07J 3/00; A61K 31/33; A61K 31/00

(52) U.S. Cl. ........................... 514/183; 514/163; 552/515; 552/516; 552/557; 552/611; 552/633; 552/635

(58) Field of Search .......................... 514/183; 552/516, 552/557, 611, 633, 635

(56) References Cited

FOREIGN PATENT DOCUMENTS

| WO 96 00235 | 1/1996 | (WO) . |
|---|---|---|
| WO 96 27658 | 9/1996 | (WO) . |
| WO 97 00884 | 1/1997 | (WO) . |
| WO 98 52965 | 11/1998 | (WO) . |
| WO 98 55498 | 12/1998 | (WO) . |

OTHER PUBLICATIONS

Byskov Et Al., "Chemical Structure of Sterols that Activate Oocyte Meiosis," Nature, vol 374, No. 6522, Apr. 1995, pp. 559–562.

Dygos Et Al., "Steroidal Ethers. Analogues of 7-Ketocholesteral," Journal of Organic Chemistry, vol. 44, No. 10, May 1979, pp. 1590–1596.

*Primary Examiner*—Sabiha N. Qazi
(74) *Attorney, Agent, or Firm*—William M. Blackstone

(57) ABSTRACT

The invention relates to 17β-aryl(arylmethyl)oxy(thio) alkyl-androstane derivatives having general formula (I), wherein $R_1$ is (H,OR), (H,OSO$_3$H) or NOR; with R being H, $(C_{1-6})$alkyl or $(C_{1-6})$acyl; each of $R_2$ and $R_3$ is independently hydrogen or $(C_{1-6})$alyl; n is 0, 1, or 2; X is O, S, S(O) or S(O)$_2$; m is 0 or 1; each of $R_4$, $R_5$ and $R_6$ is independently hydrogen, hydroxy, $(C_{1-4})$alkoxy, halogen, NR$_7$R$_8$ or $(C_{1-4})$ alkyl, optionally substituted by hydroxy, alkoxy, halogen or oxo; each of $R_7$ and $R_8$ is independently hydrogen or $(C_{1-4})$alkyl, and wherein the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$; or a pharmaceutically acceptable salt thereof. The compounds of the invention have meiosis regulating activity and can be used for the control of fertility.

(I)

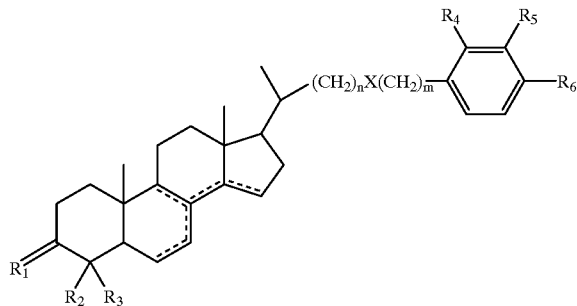

8 Claims, No Drawings

17β-ARYL(ARYLMETHYL)OXY(THIO) ALKYL-ANDROSTANE DERIVATIVES

This application is a 371 of PCT/EP98/08130, Dec. 11, 1998.

The invention relates to 17β-aryl(arylmethyl)oxy(thio) alkyl-androstane derivatives, to pharmaceutical compositions containing the same, as well as to the use of these 17β-aryl(arylmethyl)oxy(thio)alkyl-androstane derivatives for the preparation of a medicament for the control of fertility.

Sexual reproduction involves a cyclic alternation of diploid and haploid states: diploid cells divide by the process of meiosis to form haploid cells, and the haploid cells fuse in pairs at fertilization to form new diploid cells. The process of meiosis is characterized by two meiotic divisions, unique to both male and female germ cells. During the process two cell divisions, following one round of DNA replication, give rise to four haploid cells from one single diploid cell. Chromosomal crossover events, during which paternal and maternal genetic material is exchanged, occur during the prophase of the first meiotic division. At the end of the first meiotic division one member of each chromosome pair, composed of two sister chromatids is distributed to each daughter cell. The second meiotic division segregates each sister chromatide into a separate haploid cell. Male and female germ cells are subject to similar meiotic divisions but differ in the regulation of these processes.

In the male meiosis is a continuous process in germ cells derived from a population of immature germ cells, the stem cell spermatogonia. After sexual maturation of the male, spermatogonia from this stem cell population embark on meiosis. The first and second meiotic division proceed without interruption and eventually give rise to four mature spermatozoa.

In the female, primary oocytes start the first meiotic division already during the embryonic stage but they remain arrested in the prophase (dictyate stage) until the female becomes sexually mature. Meiosis resumes at the time of ovulation (egg maturation) after which the first meiotic division is completed and the second meiotic division is initiated. In most vertebrates the second meiotic division is arrested at the metaphase and only completed after fertilization. At the end of the first and of the second meiotic division the cytoplasm divides asymmetrically to produce two secondary oocytes, each with a haploid number of single chromosomes, but greatly differing in size: one is a small polar body, which eventually degenerates, and the other is a large cell containing all the developmental potential. Finally one mature ovum is produced.

The stage at which the developing oocyte is released from the ovary and is ready for fertilization differs in different species. In both invertebrates and vertebrates ovarian accessory cells respond to polypeptides (gonadotropins) produced elsewhere in the body so as to control the maturation of the oocyte and eventually (in most species) ovulation. In humans the primary oocytes of the newborn female are arrested in prophase of meiotic division I and most are surrounded by a single layer of follicle cells; such an oocyte with its surrounding cells constitute the primordial follicle. A small portion of primordial follicles sequentially begin to grow to become developing follicles: the follicle cells enlarge and proliferate to form a multilayered envelope around the primary oocyte; the oocyte itself enlarges and develops the zona pellucida, an extracellular matrix consisting largely of glycoproteins, and cortical granules, specialized secretory vesicles just under the plasma membrane in the outer region, the cortex, of the egg cytoplasm [when the egg is activated by a sperm, these cortical granules release their contents by exocytosis; the contents of the granules act to alter the egg coat so as to prevent other sperms from fusing with the egg].

The developing follicles grow continuously and some of them develop a fluid-filled cavity, or antrum, to become antral follicles. Development of such follicles is dependent on gonadotropins (mainly follicle stimulating hormone -FSH) secreted by the pituitary gland and on estrogens secreted by the follicle cells themselves. Starting at puberty, a surge of secretion by the pituitary of another gonadotropin, luteinizing hormone (LH), activates a single antral follicle to complete its development: the enclosed primary oocyte matures to complete the meiotic division I as the stimulated follicle rapidly enlarges and ruptures at the surface of the ovary, releasing the secondary oocyte within. As is the case with most mammals, the secondary oocyte is triggered to undergo division II of meiosis only if it is fertilized by a sperm.

Studies on the mechanisms controlling initiation and regulation of the meiotic process in male and female germ cells suggest a role for cyclic nucleotides in mediating meiotic arrest. Spontaneous maturation of oocytes can be prevented by compounds that maintain elevated cAMP levels [Eppig, J. and Downs, S. (1984) *Biol. Reprod.* 30: 1–11]. Purines, like adenosine or hypoxanthine, are thought to be involved in the cAMP mediated maintenance of meiotic arrest [Eppig, J., Ward-Bailey, P. and Coleman, D. (1985) *Biol. Reprod.* 33: 1041–1049]. The presence of a meiosis regulating substance in a culture system of fetal mouse gonads was first described by Byskov, A. et al (1976) *Dev. Biol.* 52: 193–200. It was suggested that the concentrations of a meiosis activating substance (MAS) and a meiosis preventing substance (MPS) regulate the meiotic process in concert [Byskov, A. et al. (1994). In *"The physiology of reproduction"*, Eds. Knobil, E. and Neill, J., Raven Press, New York]. More recently (3β,5α,20R)-4,4-dimethylcholesta-8,14,24-trien-3-ol (FF-MAS), isolated from human follicular fluid, and (3β,5α,20R)-4,4-dimethyl-cholesta-8,24-dien-3-ol, isolated from bull testes, were identified by Byskov, A. et al [(1995), *Nature* 374: 559–562] as endogenous meiosis activating substances in human and bovine, respectively. These sterols proved to be able to activate the resumption of meiosis in cultured cumulus enclosed and naked mouse oocytes.

Derivatives of the endogenous sterols, having either a saturated or an unsaturated cholestane side chain, have been disclosed in the international patent applications WO 96/00235, WO97/00883, WO97/00884 and WO98/28323 (NOVO NORDISK A/S) as meiosis regulating substances. Meiosis regulating substances are compounds that are agonists or antagonists of a naturally occurring meiosis activating substance. Thus, they might be used in the treatment of infertility or for contraception.

A drawback of the compounds described in the patent applications mentioned above is that they are prone to rapid deactivation in the body [Hall, P. F. (1985) *Vitamins and Hormones*, 42: 315], thereby restricting their therapeutic potential as fertility control agents.

A need therefore exists for regulators of the meiotic process having improved in vivo activity.

To this end the invention provides 17β-aryl(arylmethyl) oxy(thio)alkyl-androstane derivatives having the general formula I

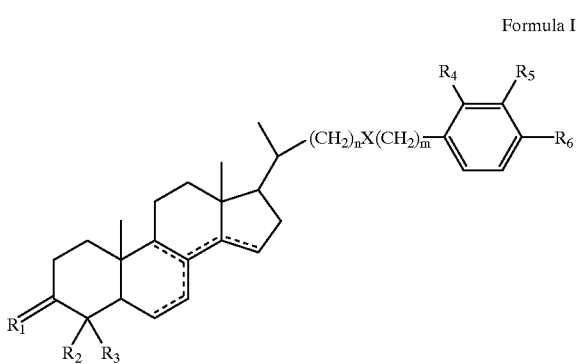

Formula I wherein
R₁ is (H,OR), (H,OSO₃H) or NOR; with R being H, (C$_{1-6}$)alkyl or (C$_{1-6}$)acyl;
each of R₂ and R₃ is independently hydrogen or (C$_{1-6}$) alkyl;
n is 0, 1 or 2;
X is O, S, S(O) or S(O)₂;
m is 0 or 1;
each of R₄, R₅ and R₆ is independently hydrogen, hydroxy, (C$_{1-4}$)alkoxy, halogen, NR₇R₈ or (C$_{1-4}$)alkyl, optionally substituted by hydroxy, alkoxy, halogen or oxo; each of R₇ and R₈ is independently hydrogen or (C$_{1-4}$)alkyl;
and wherein the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$;
or a pharmaceutically acceptable salt thereof.

It has been found that the 17β-aryl(arylmethyl)oxy(thio) alkyl-androstane derivatives having the general formula I show improved meiosis regulating activity. The invention further provides a pharmaceutical composition comprising a 17β-aryl(arylmethyl)oxy(thio)alkyl-androstane derivative having the general formula I. A further aspect of the invention resides in the use of a 17β-aryl(arylmethyl)oxy(thio) alkyl-androstane derivative having the general formula I for the manufacture of a medicament for the control of fertility.

The term (C$_{1-6}$)alkyl as used in the definition of formula I means a branched or unbranched alkyl group having 1–6 carbon atoms, like hexyl, pentyl, butyl, isobutyl, tertiary butyl, propyl, isopropyl, ethyl and methyl. Likewise, the term (C$_{1-4}$)alkyl means an alkyl group having 1–4 carbon atoms.

The term (C$_{1-6}$)acyl means an acyl group derived from a carboxylic acid having from 1–6 carbon atoms, like hexanoyl, pentanoyl, pivaloyl, butyryl, propanoyl, acetyl and formyl. Also included within the definition of (C$_{1-6}$)acyl are acyl groups derived from dicarboxylic acids, like hemiglutaroyl, hemi-succinoyl, and hemi-maloyl. A preferred (C$_{1-6}$)acyl group is hemi-succinoyl.

The term (C$_{1-4}$)alkoxy means an alkyloxy having 1–4 carbon atoms, like butyloxy, propyloxy, isopropyloxy, ethyloxy, and, preferably, methyloxy. The term halogen means F, Cl, Br or I. When halogen is a substituent at an alkyl group, like in the definition R₄, R₅ and R₆, Cl and F are preferred, F being most preferred.

It is understood that the 17β-aryl(arylmethyl)oxy(thio) alkyl-androstane derivatives of the invention have the natural configurations 5α, 9α, 10α, 13α, 14α. Preferred agonistic compounds according to the invention are the 17β-aryl (arylmethyl)oxy(thio)alkyl-androstane derivatives of formula I wherein n is 0 or 1, X is O and m is 0 or 1. More preferred are the compounds wherein in addition R₁ is (H,OR), wherein R has the previously given meaning, and the dotted lines indicate a $\Delta^{8,14}$ diene system. Among these preferred compounds those with the 3-OR substituent in the β-configuration are especially preferred. The configuration at position 20 of the 17β-aryl(arylmethyl)oxy(thio)alkyl-androstane derivatives of the invention can be either R or S. A specifically preferred agonistic compound of the invention is the 17β-aryloxyalkyl-androstane derivative (3β,5α,20R)-4,4-dimethyl-20-phenoxypregna-8,14-dien-3-ol.

Preferred antagonistic compounds according to the invention are the 17β-aryl(arylmethyl)oxy(thio)alkyl-androstane derivatives of formula I wherein n is 0 or 1, X is S, S(O) or S(O)₂ and m is 0 or 1. More preferred are the compounds wherein in addition R₁ is (H,OR), wherein R has the previously given meaning, and the dotted lines indicate a $\Delta^{8,14}$ diene system. Among these preferred compounds those with the 3-OR substituent in the β-configuration are especially preferred. The configuration at position 20 of the 17β-aryl(arylmethyl)oxy(thio)alkyl-androstane derivatives of the invention can be either R or S. A specifically preferred antagonistic compound of the invention is the 17β-arylsulfonylalkyl-androstane derivative (3β,5α,20S)-4,4,20-trimethyl-21-(phenylsulfonyl)pregna-8, 14-dien-3-ol.

The meiosis activating activity of the 17β-aryl (arylmethyl)oxy(thio)alkyl-androstane derivatives of the invention is measured in an in vitro oocyte assay as the ability to overcome the hypoxanthine maintained meiotic arrest in denuded oocytes (DO) or cumulus enclosed oocytes (CEO).

The meiosis inhibiting activity of the 17β-aryl (arylmethyl)oxy(thio)alkyl-androstane derivatives of the invention is measured in an in vitro oocyte assay as the ability to inhibit the FF-Mas or 22S-hydroxy-FF-Mas induced maturation, in hypoxanthine media, in denuded oocytes or cumulus enclosed oocytes, respectively. The compounds can be used to stimulate or inhibit meiosis in both male and female and thus can be used as fertility regulating agents. Fertility regulation comprises contraception and infertility treatment.

For female contraception a 17β-aryl(arylmethyl)oxy(thio) alkyl-androstane derivative according to formula I can be used for induction of premature maturation of oocytes which are still inside the ovary, before the naturally occurring gonadotropin surge [reduced fertility by inducing premature maturation of oocytes has been demonstrated in rats by Mattheij, J. et al (1993), Gynecol. Obstet. Invest. 36: 129–135]. On in vivo administration the compounds of the invention specifically affects germ cells and therefore have the advantage of maintenance of endogenous hormonal levels and subsequently maintenance of normal cycle length. Such a contraceptive method will not cause unwanted side-effects sometimes associated with steroidal contraception (e.g. thrombosis, mood, unscheduled bleeding, malignant breast disease). In this connection it is important to note that the compounds of the invention do no bind to steroid receptors since no binding was found for progesterone receptor, androgen receptor, estrogen receptor and glucocorticoid receptor. Furthermore, it was found that compounds did not have an effect on steroid synthesis or metabolism in human adrenal cells at a dose level which induces oocyte maturation in vitro.

A further advantage of the 17β-aryl(arylmethyl)oxy(thio) alkyl-androstane derivatives of the invention is their inability to induce maturation in incompetent oocytes (isolated from pre-antral follicles), which indicates that the compounds will not affect the entire oocyte reserve in the ovaries. Only oocytes from antral follicles (competent oocytes) can be induced to mature by the compounds of the invention. 17β-Aryl(arylmethyl)oxy(thio)alkyl-androstane derivatives of the invention acting as inhibitors of the FF-Mas induced oocyte maturation can be used for female contraception by inhibition of the naturally induced oocyte maturation caused by the gonadotrophin surge. These compounds may induce an ovulated not-matured oocyte which cannot be fertilized.

For treatment of female infertility caused by the absence of mature oocytes the compounds of the invention can be administered in vivo to timely stimulate the maturation of competent oocytes.

The compounds of the invention can also be used for suppletion of culture media for in vitro fertilization procedures in order to improve oocyte quality.

For male contraception the compounds of the invention can be administered in vivo to inhibit the spermatogenesis.

For treatment of male infertility caused by a shortage of the number of mature spermatozoa the compounds of the invention can be administered in vivo to stimulate the maturation of spermatogonia.

The 17β-aryl(arylmethyl)oxy(thio)alkyl-androstane derivatives of this invention have the natural configurations 5α, 9α, 10β, 13β, 14α, 17β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

Compounds according to formula I wherein X is S(O) may exist as a diastereoisomeric sulfoxide pair, due to the presence of the optically active sulfur atom. Both the diastereoisomeric mixture and the separate isomers are included in the present invention.

For therapeutic use, salts of the compounds of formula I are those wherein the counterion is pharmaceutically acceptable. However, salts of the acids according to formula I [i.e. compounds wherein $R_1$ is (H,OSO$_3$H)] may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of formula I or a pharmaceutically acceptable salt thereof, also referred to herein as the active ingredient, may be administered enterally or parenterally. The exact dose and regimen of administration of the active ingredient, or a pharmaceutical composition thereof, will necessarily be dependent upon the therapeutic effect to be achieved (treatment of infertility; contraception), and will vary with the particular compound, the route of administration, and the age and condition of the individual subject to whom the medicament is to be administered. In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, like in IVF applications, the compounds of the inventions are to be used in the incubation media in a concentration of approximately 0.01–5 μg/ml.

The present invention thus also relates to pharmaceutical compositions comprising a 17β-aryl(arylmethyl)oxy(thio) alkyl-androstane derivative according to formula I in admixture with pharmaceutically acceptable auxiliaries, and optionally other therapeutic agents. The auxilliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: Pharmaceutical Preparations and Their Manufacture). Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurised aerosols, nebulisers or insufflators.

The 17β-aryl(arylmethyl)oxy(thio)alkyl-androstane derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO N.V.).

The compounds of the invention may be produced by various methods known in the art of organic chemistry in general, and especially in the art of the chemistry of steroids (see, for example: Fried, J. and Edwards, J. A., "*Organic Reactions in Steroid Chemistry*", Volumes I and II, Van Nostrand Reinhold Company, New York, 1972). A suitable method for the preparation of compounds of formula I is the condensation of a compound of general formula II, Formula II

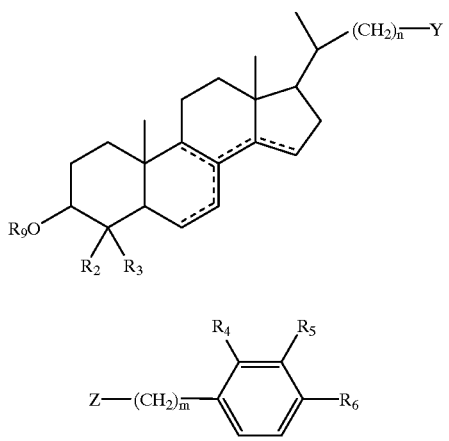

Formula III wherein $R_2$ and $R_3$ are independently hydrogen or $(C_{1-6})$ alkyl, $R_9$ is a hydroxy-protecting group such as an acyl group, like an acetyl group, a benzoyl group or a pivaloyl group, or an alkoxyalkyl group, like an ethoxyethyl group or a tetrahydropyranyl (THP) group, n is 0, 1 or 2, and wherein the dotted lines represent a $\Delta^7$ or a $\Delta^8$ double bond, or a pair of conjugated double bonds selected from $\Delta^{7,14}$, $\Delta^{8,14}$, or $\Delta^{6,8(14)}$, and wherein Y is OH, with a (thio)phenol derivative or benzyl alcohol(mercaptan) derivative having formula III, wherein $R_4$, $R_5$, and $R_6$ have the previously given meaning, Z is OH or SH and m is 0 or 1, or the reaction of a compound according to formula II wherein Y is a halogen, preferably bromide, or a leaving group like tosyloxy or mesyloxy, with a compound according to formula III wherein Z is OH or SH, or the reaction of a compound according to formula II wherein Y is OH or SH with a compound according to formula III (m=1) wherein Z is a halogen, preferably bromide, or a leaving group like tosyloxy or mesyloxy, whereafter a 17-aryl(arylmethyl)thioalkyl-androstane derivative is optionally oxidized to the corresponding sulfoxide (X=SO) or sulfone (X=SO$_2$) derivative, after which any remaining protecting groups are removed, and the 3-OH group of the product is optionally converted to a 3-OR group, wherein R has the meaning as previously defined, or wherein the 3-OH group is oxidized and the resulting 3-keto-group converted to NOR, wherein R has the meaning as previously defined.

The condensation reactions between compounds having formula II and compounds having formula III are carried out using methods known in the art. For instance, compounds of formula I (X=O,S; n=0,1,2; m=0) can be prepared by means of a Mitsunobu reaction between a compound of formula II wherein Y is OH with an unsubstituted or suitably substituted phenol or thiophenol derivative [a compound having formula III (m=0)] [see Hughes, D. L., Organic Reactions 42, 335 (1992)]. This reaction can be carried out using a dialkyl azodicarboxylate, like diethyl azodicarboxylate or diisopropyl azodicarboxylate, or other azodicarbonyl derivatives, like 1,1'-(azodicarbonyl)dipiperidine [Tsunoda, T. et al, Tetrahedron Lett. 34, 1639 (1993)]. Phosphines which can be used are: triarylphosphines like triphenylphosphine, trialkylphosphines like tributylphosphine, or trialkylphosphites like trimethylphosphite.

The condensation reaction can also be carried out by means of an etherification reaction, i.e. by reaction of compounds of general formula II, wherein Y is a leaving group such as bromide, iodide, tosyloxy and mesyloxy, with a suitably substituted phenol or thiophenol derivative, which is previously converted to the lithium, sodium or potassium salt [see e.g. Meerwein, H., Methoden der Organischen Chemie (Houben-Weyl), Band VI/3, p. 1, Georg Thieme Publishers, Stuttgart, 1965; Yin, J. et al, Tetrahedron Lett. 38, 5953 (1997) and references cited therein]. Compounds of formula I (X=O,S; n=0,1,2; m=1) can be prepared analogously by means of an etherification reaction between a compound of formula II wherein Y is a leaving group such as bromide, iodide, tosyloxy and mesyloxy, with a suitably substituted benzyl alcohol or benzyl marcaptan derivative, which is previously converted to the lithium, sodium or potassium salt. In this case, the etherification reaction can also be carried out in the opposite direction, i.e. by reaction between a metallated (Li, Na, K) compound of general formula II (Y=OH,SH) and a compound of formula IIII (m=1) in which Z is a leaving group such as bromide, iodide, tosyloxy and mesyloxy.

Compounds of general formula I wherein X is S(O) or S(O)$_2$ can be prepared from compounds of formula I wherein X is S by oxidation using agents capable of converting a thio ether into a sulfoxide or a sulfone, e.g. H$_2$O$_2$ and the like [see Varma, R. S. et al, Tetrahedron Lett. 38, 6525 (1997) and references cited therein]. Compounds of general formula I (X=S(O)$_2$; n=1,2; m=0) can also be prepared directly by reaction of compounds of general formula II in which Y is a leaving group such as bromide, iodide, tosyloxy and mesyloxy, with an unsubstituted or suitably substituted benzenesulfinic acid derivative, which is previously converted to the sodium or potassium salt [see Trost, B. M. et al, J. Am. Chem. Soc. 105, 5075 (1983)].

A convenient starting material for the preparation of compounds having formula II (n=0) is (3β)-3-hydroxypregn-5-en-20-one (compound 1; see Scheme 1) which is commercially available. A possible synthesis route (specific examples are exemplified in Example 1 and 2, and Scheme 1 and 2) starts with the protection of the hydroxy group at C-3 by an ether type protecting group, e.g. an ethoxyethyl ether or a THP ether, or by a silyl ether. These and other suitable protective groups are known in the art, e.g. from Greene, T. W. and Wuts, P. G. M.: Protective groups in Organic Synthesis, Wiley, New York, 1991.

In a second step, the carbonyl function at C-20 is reduced to a hydroxy group. The reduction can be carried out using hydride reducing agents, like lithium aluminium hydride, sodium borohydride, and the like, in which case the 20R isomer is mainly formed [Antia, N. J. et al, J. Chem. Soc. 1218 (1954)]. The reduction can also be carried out using alkalimetals in alkanols [Meystre, C. Helv. Chim. Acta 29, 33 (1946)] or with boranes [Midland, M. M. et al, J. Amer. Chem. Soc. 105, 3725 (1983)], which lead to the predominant formation of the 20S isomer.

As an alternative the 3-protected pregn-5-ene-3,20-diols can be prepared by hydroboration of suitably protected pregna-5, 17(20)-dien-3-ol derivatives [Murayama, E. et al, Chem. Pharm. Bull. 34, 4410 (1986); Yoshizawa, I. et al, Chem. Pharm. Bull. 31, 3819 (1983)]. The hydroxy group at C-20 is converted to an ester, e.g. an acetate ester or a benzoate ester and the like and the 3-hydroxy function is deprotected. The latter is oxidized to a carbonyl group, which can be accomplished by an Oppenauer oxidation or a Swern oxidation, or by using chromium(VI) reagents, e.g. Jones reagent, pyridinium dichromate, pyridium chlorochromate or other oxidizing agents known in the art. The hydroxy group at C-20 is deprotected by saponification and then reprotected as a silyl ether, e.g. a diisopropylsilyl ether, a t-butyldimethylsilyl ether, or a t-butyldiphenylsilyl ether.

Optionally, the resulting product can now be mono- or dialkylated at C-4, for instance, it can be dialkylated with methyl. Alkylation can be performed using standard procedures [such as potassium t-butoxide/methyliodide in t-butanol/-tetrahydrofuran: Dolle, R. E. et al, J. Org. Chem. 51, 4047 (1986)], it can also be accomplished by other techniques, e.g. lithium diisopropylamide/methyliodide in tetrahydrofuran, and similar methods known in the art. Alternatively, the $\Delta^4$ compound can be converted to a $\Delta^5$ derivative by reaction with a base followed by quenching with water [Jones, J. B. et al, Can. J. Chem. 46, 1459 (1968)]. In both cases, the carbonyl group at C-3 is reduced to hydroxy. Reducing agents which can be used include lithium aluminium hydride, sodium borohydride, or other hydride reducing agents known in the art. The resulting 3-hydroxy compound is protected as an ester, e.g. an acetate ester, a benzoate ester, or a pivalate ester and the like.

The $\Delta^5$ system can now be converted to a $\Delta^{5,7}$-diene system by the sequence: bromination at C-7 followed by dehydrobromination. The bromination reaction can be carried out thermally [Schroepfer, G. J., Jr., et al, Chem. Phys. Lipids 47, 187 (1988)] or photochemically [Prelle, A. et al, Heterocycles 28, 333 (1989)]. In both cases, brominating agents which can be used are N-bromosuccinimide, 1,3-dibromo-5,5-dimethylhydantoin and the like. Dehydrobrominating agents include N,N-diisopropylethylamine, 2,4,6-trimethylpyridine, trimethylphosphite, tetrabutylammonium fluoride and others.

The $\Delta^{5,7}$ diene system can be converted to a $\Delta^{7,14}$ diene system, a $\Delta^{8,14}$ diene system, or a $\Delta^{6,8(14)}$ diene system. Methods used are known in the art. For conversion to the $\Delta^{7,14}$ derivative, see e.g. Wilson, W. K. et al, J. Org. Chem. 53, 1713 (1988). For conversion to the $\Delta^{8,14}$ derivative, see e.g. Schroepfer, G. J., Jr., et al, Chem. Phys. Lipids 47, 187 (1988) or Dolle, R. E. et al, J. Org. Chem. 53, 1563 (1988). For conversion to the $\Delta^{6,8(14)}$ derivative, see e.g. Kaneko, C. et al, Chem. Pharm. Bull. 26, 3582 (1978). $\Delta^7$ Compounds are obtained from the $\Delta^{5,7}$ diene system by reduction with lithium in liquid ammonia [Lederer, F. et al, Bull. Soc. Chim. Fr. 1295 (1965)] or by hydrogenation. Hydrogenation catalysts which can be used include Raney nickel [Gautschi, F. et al, J. Biol. Chem. 233, 1343 (1958)], Wilkinson's catalyst [Canonica, L. et al, Steroids 11, 287 (1968)] and others. $\Delta^8$ Derivatives are prepared from $\Delta^{8,14}$ dienes by the sequence: selective hydroboration of the $\Delta^{14}$ double bond followed by deoxygenation of the 15-hydroxy compound produced [Dolle, R. E. et al, J. Amer. Chem. Soc. 111, 278 (1989)].

Deprotection of the hydroxy group at C-20 (if necessary, in some cases manipulation of the $\Delta^{5,7}$ system can be accompanied by deprotection of that group) results in the unsaturated pregna-3,20-diol derivatives of formula II (Y=OH; n=0) in which the 3-hydroxy function is protected as an ester ($R_9$=acyl) (e.g. compound 13a; Scheme 1).

Unsaturated pregna-3,20-diol derivatives of formula II (Y=OH; n=0) in which the 3-hydroxy function is protected as an alkoxyalkyl ether (e.g. compound 19b; Scheme 2) can be obtained from compounds of formula II [Y=(protected) OH; n=0; $R_9$=acyl] as follows: the 20-hydroxy function is protected as a silyl ether as described before (if necessary), the ester function at C-3 is removed by reduction with lithium aluminium hydride, or by other hydride reducing agents known in the art, whereafter the 3-hydroxy group is reprotected as an alkoxyalkyl ether, e.g. an ethoxyethyl ether or a tetrahydropyranyl ether. Finally, treatment with a fluoride agent, e.g. potassium fluoride, tetrabutylammonium fluoride or other reagents known in the art then results in the formation of the unsaturated pregna-3,20-diol derivatives of formula II (Y=OH; n=0) in which the 3-hydroxy function is protected as an alkoxyalkyl ether.

Compounds having formula II (Y=OH; n=1) can be obtained from e.g. (20S)-21-hydroxy-20-methylpregn-4-en-3-one [Trost, B. M. et al, J. Amer. Chem. Soc. 105, 5075 (1983)] by a sequence of reactions analogous to that described above.

Compounds having formula II (Y=OH; n=2) can be prepared from compounds of formula II (Y=OH; n=1) by homologation, e.g. by the reaction sequence: conversion of the 21-hydroxy group to a leaving group, reaction with potassium cyanide, reduction of the carbonitrile group to the corresponding carboxaldehyde group, reprotection of the 3-hydroxy group as an alkoxyalkyl ether, like an ethoxyethyl group or a THP group and, finally, reduction to the 23-hydroxy derivative. As an alternative a one-carbon homologation starting with the corresponding 20-carboxaldehyde can be accomplished via a Wittig condensation with $(Ph)_3P$=CHOMe and hydrolysis of the intermediate enol ether. Techniques for homologation are well known in the art, see e.g. Mathieu, J. et al: Formation of C—C Bonds, Vol. I–III, Georg Thieme Publishers, Stuttgart, 1973.

Compounds having formula II (Y=SH; n=0,1,2) can be prepared from compounds of formula II (Y=OH; n=0,1,2) by means of a Mitsunobu reaction with thioacetic acid followed by conversion to the thiol derivative by reduction or saponification [see Hughes, D. L., Organic Reactions 42, 335 (1992)]. Alternatively, they can be prepared by reaction of compounds of general formula II in which Y is a leaving group such as bromide, iodide, tosyloxy and mesyloxy, with thiourea followed by reaction with a base, like sodium hydroxide or potassium hydroxide [see e.g. Allewaert, K. et al, Bioorganic & Med. Chem. Lett. 3, 1859 (1993)].

Compounds of formula I in which $R_1$ is (H,OH) may serve as starting material for the synthesis, using methods known in the art, of compounds of formula I in which $R_1$ is (H,OR), (H,OSO$_3$H) or NOR, and R is H, ($C_{1-6}$)alkyl, or ($C_{1-6}$)acyl.

The invention is further illustrated with reference to the following schemes and examples.

Scheme 1

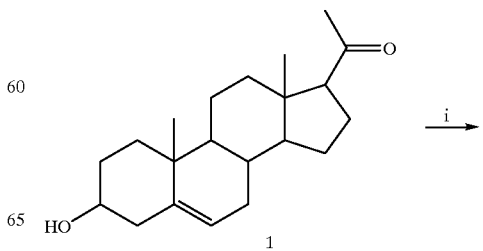

1

11
-continued
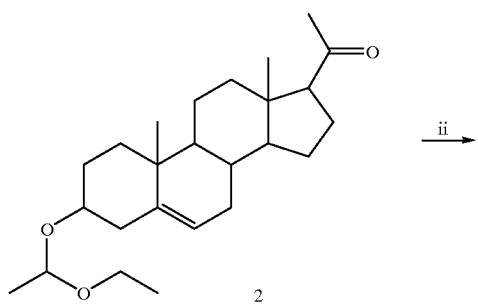
2
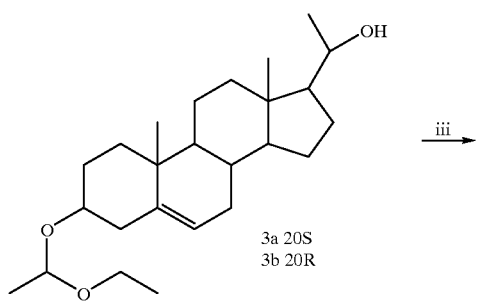
3a 20S
3b 20R
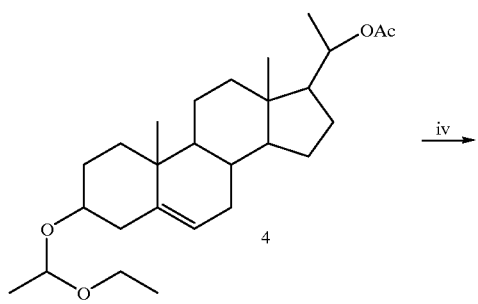
4
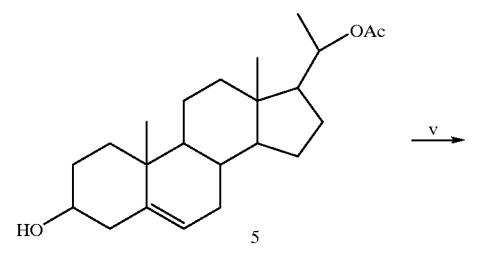
5
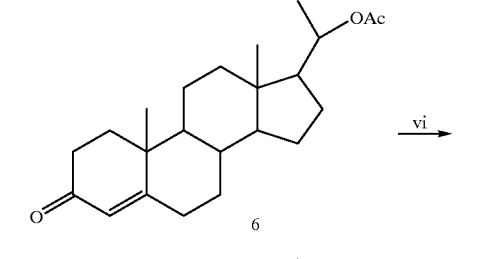
6
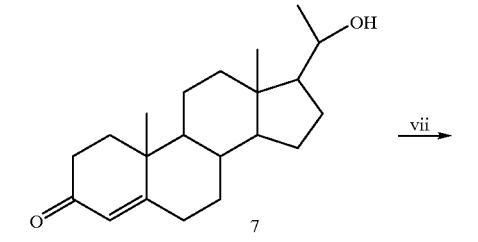
7
12
-continued
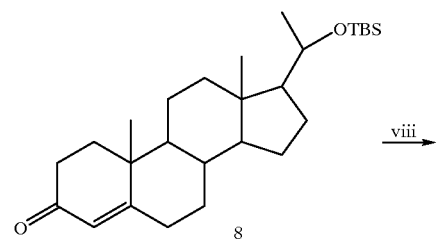
8
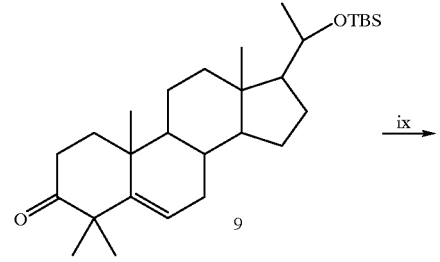
9
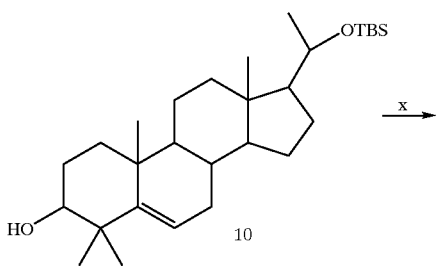
10
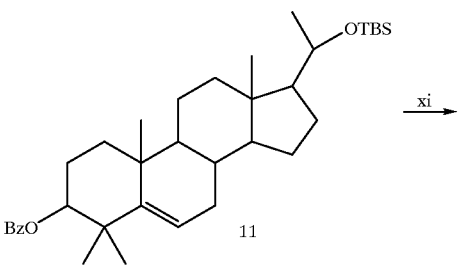
11
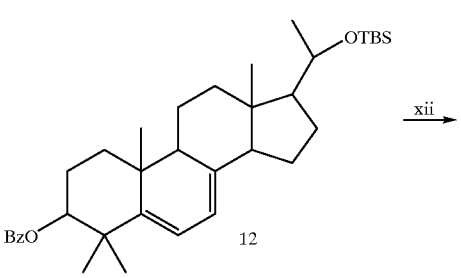
12
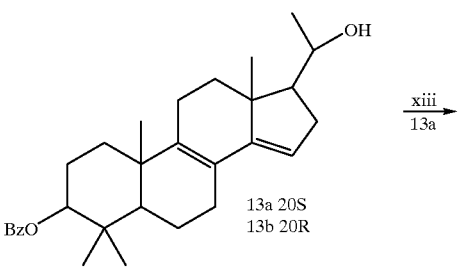
13a 20S
13b 20R

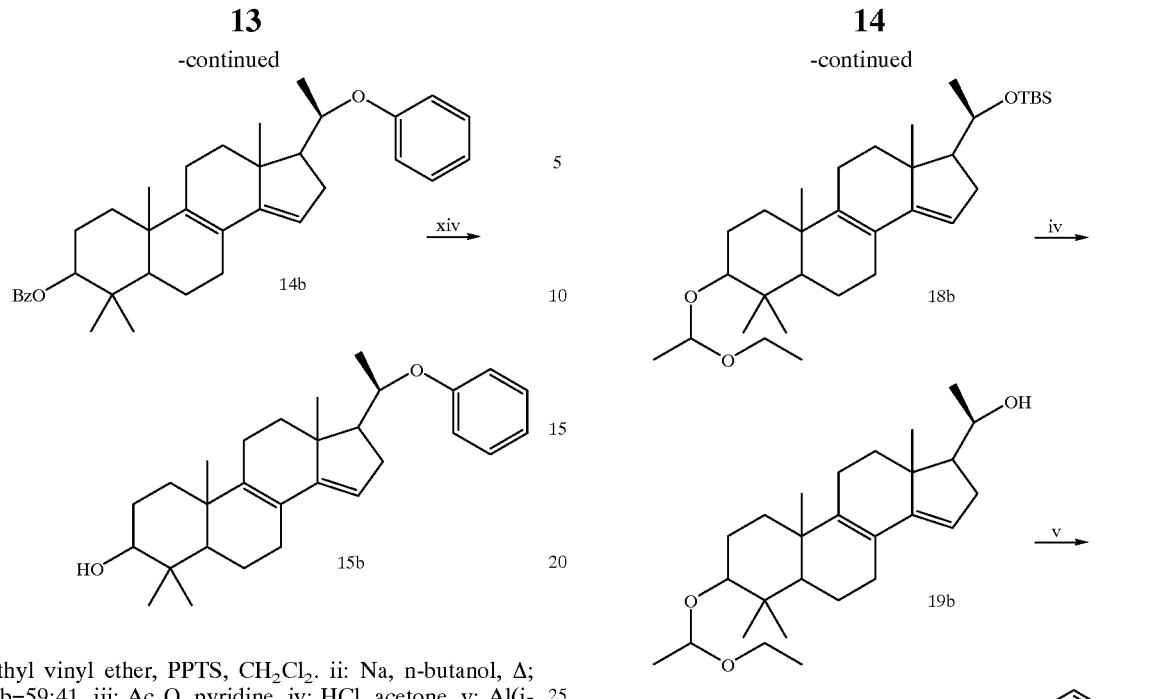

i: Ethyl vinyl ether, PPTS, $CH_2Cl_2$. ii: Na, n-butanol, Δ; 3a:3b=59:41. iii: $Ac_2O$, pyridine. iv: HCl, acetone. v: Al(i-OPr)$_3$, 2-butanone, toluene, Δ. vi: KOH, MeOH, THF, $H_2O$. vii: t-Butyldimethylsilyl chloride (TBSCl), imidazole, DMF. viii: MeI, t-BuOK, t-BuOH, THF, 45° C. ix: LiAlH$_4$, THF. x: BzCl, pyridine. xi: 1) NBS, cyclohexane, toluene, Δ. 2) EtN(i-Pr)$_2$, toluene, Δ. xii: HCl, $H_2O$, EtOH, toluene, Δ. xiii: 1,1'-(Azodicarbonyl)dipiperidine, triphenylphosphine, phenol, THF. xiv: LiAlH$_4$, THF.

Scheme 2

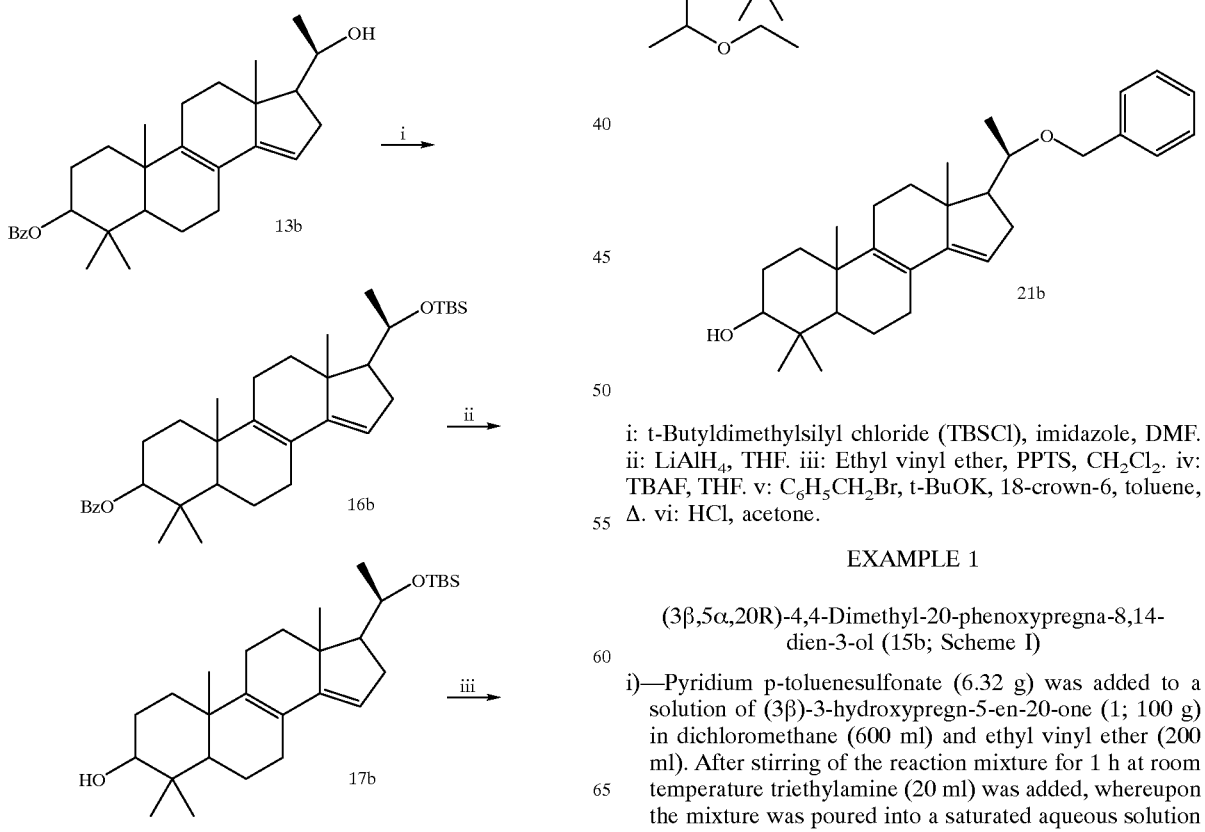

i: t-Butyldimethylsilyl chloride (TBSCl), imidazole, DMF. ii: LiAlH$_4$, THF. iii: Ethyl vinyl ether, PPTS, $CH_2Cl_2$. iv: TBAF, THF. v: $C_6H_5CH_2Br$, t-BuOK, 18-crown-6, toluene, Δ. vi: HCl, acetone.

EXAMPLE 1

(3β,5α,20R)-4,4-Dimethyl-20-phenoxypregna-8,14-dien-3-ol (15b; Scheme I)

i)—Pyridium p-toluenesulfonate (6.32 g) was added to a solution of (3β)-3-hydroxypregn-5-en-20-one (1; 100 g) in dichloromethane (600 ml) and ethyl vinyl ether (200 ml). After stirring of the reaction mixture for 1 h at room temperature triethylamine (20 ml) was added, whereupon the mixture was poured into a saturated aqueous solution of sodium hydrogen carbonate (1 l). The product was extracted into dichloromethane; the combined organic phases were washed with brine, dried over sodium sulfate, and concentrated under reduced pressure to give (3β)-3-[(1-ethoxyethyl)oxy]pregn-5-en-20-one (2; 125.6 g), which was used in the following step without further purification.

ii)—Sodium (8.98 g) was added in small portions in the course of 2 h to a refluxing solution of (3β)-3-[(1-ethoxyethyl)oxy]pregn-5-en-20-one (20 g) in dry n-butanol (587 ml). Heating was continued for another 2 h; then the reaction mixture was cooled and poured into a saturated aqueous solution of sodium hydrogen carbonate (1.5 l). The product was extracted into ethyl acetate; the combined organic phases were washed with brine, dried over sodium sulfate, and concentrated under reduced pressure. Column chromatography of the crude product afforded (3β,20R)-3-[(1-ethoxyethyl)oxy]pregn-5-en-20-ol (compound 3b; 5.08 g) and (3β,20S)-3-[(1-ethoxyethyl)oxy]pregn-5-en-20-ol (compound 3a; 7.21 g).

iii)—A solution of (3β,20S)-3-[(1-ethoxyethyl)oxy]pregn-5-en-20-ol (compound 3a; 56.9 g) in a mixture of dry pyridine (144 ml) and acetic anhydride (72.4 ml) was stirred at room temperature for 18 h. Water (482 ml) was added and stirring was continued for another 1 h. The product was extracted into ethyl acetate; the combined organic phases were washed with a saturated aqueous solution of sodium hydrogen carbonate and with brine, dried over sodium sulfate, and concentrated under reduced pressure to give (3β,20S)-3-[(1-ethoxyethyl)oxy] pregn-5-en-20-ol acetate (compound 4a; 66.1 g) which was used in the following step without further purification.

iv)—A solution of (3β,20S)-3-[(1-ethoxyethyl)oxy]pregn-5-en-20-ol acetate (66.1 g) in acetone (1330 ml) was treated with a 4 M aqueous solution of hydrochloric acid (13.2 ml). The reaction mixture was stirred for 45 minutes and subsequently poured into a mixture of water (3 l) and a saturated aqueous solution of sodium hydrogen carbonate (500 ml). The resulting precipitate was collected by filtration and then dissolved in dichloromethane. The filtrate was extracted with ethyl acetate. The dichloromethane and ethyl acetate solutions were washed with a saturated aqueous solution of sodium hydrogen carbonate and with brine, dried over sodium sulfate, and concentrated under reduced pressure to give (3β,20S)-pregn-5-ene-3,20-diol 20-acetate (compound 5a; 53.5 g), which was used in the following step without further purification.

v)—Aluminium isopropoxide (18.1 g) was added to a solution of (3β,20S)-pregn-5-ene-3,20-diol 20-acetate (21.9 g) in dry toluene (252 ml) and dry 2-butanone (156 ml). The mixture was heated under reflux for 2 hours, then cooled, whereupon a solution of potassium sodium tartrate tetrahydrate (91.4 g) in water (90 ml) was added. The mixture was stirred for 30 min. and filtered. The filtrate was poured into brine and the product extracted into ethyl acetate. The combined organic phases were washed with brine, dried over sodium sulfate, and concentrated under reduced pressure. Column chromatography afforded (20S)-20-(acetyloxy)pregn-4-en-3-one (compound 6a; 17.9 g).

vi)—Potassium hydroxide (22.5 g) was added to a solution of (20S)-20-(acetyloxy)pregn-4-en-3-one (17.9 g) in tetrahydrofuran (418 ml), methanol (380 ml) and water (125 ml). The mixture was stirred for 3 h at room temperature and then poured into water (2 l). The product was extracted into ethyl acetate; the combined organic phases were washed with brine, dried over sodium sulfate, and concentrated under reduced pressure. Column chromatography afforded (20S)-20-hydroxypregn-4-en-3-one (compound 7a; 35.4 g).

vii)—t-Butyldimethylsilyl chloride (39.6 g) was added to a solution of (20S)-20-hydroxypregn-4-en-3-one (36.3 g) and imidazole (53.5 g) in dry N,N-dimethylformamide (345 ml). The reaction mixture was stirred for 2.5 hours at room temperature and then poured into water. The product was extracted into ethyl acetate. The combined organic phases were washed with water and brine and dried over sodium sulfate. Column chromatography afforded (20S)-20-[[(1,1-dimethylethyl)dimethylsilyl]oxy]pregn-4-en-3-one (compound 8a; 41.6 g).

viii)—Potassium t-butoxide (46.3) was added to a solution of (20S)-20-[[(1,1-dimethylethyl)dimethylsilyl]oxy] pregn-4-en-3-one (40.6 g) in dry t-butanol (1000 ml) and dry tetrahydrofuran (146 ml). After heating the mixture at 45° C. for 10 min., iodomethane (52.4 ml) was added. The reaction mixture was heated at the same temperature overnight and then poured into water (2 l). The product was extracted into ethyl acetate; the combined organic phases were washed with brine and dried over sodium sulfate. Column chromatography afforded (20S)-20-[[(1,1-dimethylethyl)dimethylsilyl]oxy]-4,4-dimethylpregn-5-en-3-one (compound 9a; 40.7 g).

ix)—A solution of compound 9a (39.4 g) in dry tetrahydrofuran (400 ml) was added dropwise to an ice-cooled suspension of lithium aluminium hydride (9.81 g) in tetrahydrofuran (490 ml). The mixture was stirred at room temperature for 1 h. The reaction was cooled to 0° C., and then quenched with a saturated aqueous solution of sodium sulfate. The reaction mixture was filtered over celite and the filtrate concentrated under reduced pressure to give (3β,20S)-20-[[(1,1-dimethylethyl)dimethylsilyl] oxy]-4,4-dimethylpregn-5-en-3-ol (compound 10a; 38.9 g), which was used in the following step without further purification.

x)—Benzoyl chloride (19.9 ml) was added in 5 min. to an ice-cooled solution of (3β,20S)-20-[[(1,1-dimethylethyl) dimethylsilyl]oxy]-4,4-dimethylpregn-5-en-3-ol (38.9 9) in dry pyridine (395 ml). The reaction mixture was stirred for 2 h at room temperature and then poured into ice-water (2 l). The resulting suspension was stirred overnight and filtered; the residue was washed with water of 40–50° C. (1.5 l) and then dissolved in dichloromethane. The dichloromethane solution was washed with brine, dried over sodium sulfate, and concentrated under reduced pressure. Column chromatography afforded (3β,20S)-20-[[(1,1-dimethylethyl)dimethylsilyl]oxy]-4,4-dimethylpregn-5-en-3-ol benzoate (compound 11a; 45.9 g).

xi)—A mixture of (3β,20S)-20-[[(1,1-dimethylethyl) dimethylsilyl]oxy]-4,4-dimethylpregn-5-en-3-ol benzoate (44.6), dry toluene (394 ml), dry cyclohexane (394 ml) and N-bromosuccinimide (17.8 g) was heated at reflux temperature for 10 min. The reaction mixture was cooled, another portion of N-bromosuccinimide (17.8 g) was added, and reflux was continued for another 10 min. The reaction mixture was cooled, a saturated aqueous solution of sodium thiosulfate (802 ml) was added and the resulting mixture was stirred for 30 min. The organic phase and the aqueous phase were separated and the latter extracted two times with toluene. The combined organic phases were dried over sodium sulfate and concentrated under reduced pressure. A solution of the crude product thus obtained in dry toluene (1381 ml) and N,N- diisopropylethylamine (138 ml) was heated under reflux for 1.5 h. Then it was cooled and washed with a saturated aqueous solution of sodium hydrogen carbonate, a saturated aqueous solution of ammonium chloride and with brine, the aqueous phase each time being extracted with ethyl acetate. The combined toluene and ethyl acetate solutions were dried over sodium sulfate and concentrated under reduced pressure. Column chromatography afforded (3β,20S)-20-[[(1,1-dimethylethyl)dimethylsilyl]oxy]-4,4-dimethylpregna-5,7-dien-3-ol benzoate (compound 12a; 40.0 g).

xii)—A mixture of compound 12a (36.6 g), toluene (91 ml), ethanol (622 ml; 96%) and concentrated hydrochloric acid (91 ml) was heated under reflux for 4 h. The mixture was cooled and poured into a saturated aqueous solution of sodium hydrogen carbonate (1 l). The product was extracted into ethyl acetate, the combined organic phases were washed with a saturated aqueous solution of sodium hydrogen carbonate and with brine, dried over sodium sulfate, and concentrated under reduced pressure. Column chromatography and crystallization afforded (3β,5α,20S)-4,4-dimethylpregna-8,14-diene-3,20-diol 3-benzoate (compound 13a; 7.89 g) and (3β,5α,20S)-4,4-dimethylpregna-6,8(14)-diene-3,20-diol 3-benzoate (3.69 g).

xiii)—1,1'-(Azodicarbonyl)dipiperidine (5.54 g) was added to an ice-cooled solution of compound 13a (2.0 g), triphenylphosphine (5.76 g), and phenol (2.06 g) in dry THF (10 ml). After 5 min. stirring dry THF (60 ml) was added and the reaction mixture was stirred for 2 h at room temperature. Then it was poured into heptane (100 ml); the resulting mixture was filtered and the filtrate was concentrated under reduced pressure. Column chromatography afforded (3β,5α,20R)4,4-dimethyl-20-phenoxypregna-8,14-dien-3-ol benzoate (compound 14b), together with the elimination products (3β,5α)-4,4-dimethylpregna-8,14,17(20)-trien-3-ol benzoate and (3β,5α)-4,4-dimethylpregna-8,14,20-trien-3-ol benzoate (2.80 g totally). The product was used in the following step without further purification.

xiv)—Following a procedure analogous to that of step ix, the products of the previous step (2.80 g) were converted to the 3-hydroxy compounds to give, after column chromatography and crystallization, (3β,5α,20R)-4,4-dimethyl-20-phenoxypregna8,14-dien-3-ol (compound 15b, 0.049 g). M.p. 135–140° C.; $[\alpha]_D^{20}$=−30.4° (c=0.5, dioxane).

EXAMPLE 2

(3β,5α,20R)-4,4-Dimethyl-20-(phenylmethoxy)pregna-8,14-dien-3-ol (21b; Scheme 2)

Starting from (3β,5α,20R)-4,4-dimethylpregna-8,14-diene-3,20-diol 3-benzoate (compound 13b), which was prepared from (3β,20R)-3-[(1-ethoxyethyl)oxy]pregn-5-en-20-ol (compound 3b; Example 1, step ii) using reaction steps analogous to those described under iii—xii of Example 1 for (3β,5α,20S)-4,4-dimethylpregna-8,14-diene-3,20-diol 3-benzoate (compound 13a), the title compound was prepared as follows:

i)—Following a procedure analogous to that of step vii of Example 1, (3β,5α,20R)-4,4-dimethylpregna-8,14-diene-3,20-diol 3-benzoate (compound 13b, 15.2 g) was converted to (3β,5α,20R)-20-[[(1,1-dimethylethyl)dimethylsilyl]oxy]-4,4-dimethylpregna-8,14-dien-3-ol benzoate (compound 16b; 23.1 g).

ii)—Following a procedure analogous to that of step ix of Example 1, (3β,5α,20R)-20-[[(1,1-dimethylethyl)dimethylsilyl]oxy]-4,4-dimethylpregna-8,14-dien-3-ol benzoate (23.1 g) was converted to (3β,5α,20R)-20-[[(1,1-dimethylethyl)dimethyl-silyl]oxy]-4,4-dimethylpregna-8,14-dien-3-ol (compound 17b; 19.7 g).

iii)—Following a procedure analogous to that of step i of Example 1 compound 17b (15.3 g) was converted to (3β,5α,20R)-20-[[(1,1-dimethylethyl)dimethylsilyl]oxy]-3-[(1-ethoxyethyl)oxy]-4,4-dimethylpregna-8,14-diene (compound 18b; 16.4 g).

iv)—A solution of (3β,5α,20R)-20-[[(1,1-dimethylethyl)dimethylsilyl]oxy]-3-[(1-ethoxyethyl)oxy]-4,4-dimethylpregna-8,14-diene (18b; 16.4 g) in a 1 M solution of tetrabutylammonium fluoride in tetrahydrofuran (42 ml) was stirred at 50° C. for 6 h and then at room temperature for 24 h. The reaction mixture was poured into water and the product was extracted into ethyl acetate. The combined organic phases were washed with brine and concentrated under reduced pressure. Column chromatography afforded (3β,5α,20R)-3-[(1-ethoxyethyl)oxy]-4,4-dimethylpregna-8,14-dien-20-ol (compound 19b; 10.6 g).

v)—A mixture of (3β,5α,20R)-3-[(1-ethoxyethyl)oxy]-4,4-dimethylpregna-8,14-dien-20-ol (19b; 0.80 g), dry toluene (56 ml), potassium t-butoxide (2.76 g), 18-crown-6 (0.48 g) and benzyl bromide (1.13 ml) was heated at 70° C. for 1 h. After cooling, the reaction mixture was poured into water and the product extracted into ethyl acetate. The combined organic phases were washed with water and with brine, dried over sodium sulfate, and concentrated under reduced pressure to give (3β,5α,20R)-3-[(1-ethoxyethyl)oxy]-4,4-dimethyl-20-(phenylmethoxy)pregna-8,14-diene (compound 20b; 1.92 g), which was used in the following step without further purification.

vi)—Following a procedure analogous to that of step iv of Example 1, (3β,5α,20R)-3-[(1-ethoxyethyl)oxy]-4,4-dimethyl-20-(phenylmethoxy)pregna-8,14-diene (compound 20b; 1.92 g), was converted to (3β,5α,20R)-4,4-dimethyl-20-(phenylmethoxy)pregna-8,14-dien-3-ol (compound 21b; 0.54 g). M.p. 138–143° C.; $[\alpha]_D^{20}$=−46.8° (c=0.5, dioxane).

EXAMPLE 3

Starting from (3β,5α,20R)-3-[(1-ethoxyethyl)oxy]-4,4-dimethylpregna-8,14-dien-20-ol (compound 19b) described under iv of Example 2, and using reaction steps analogous to those described under v and vi of Example 2, the following compounds were prepared:

A) (3β,5α,20R)-20-[(2-Fluorophenyl)methoxy]-4,4-dimethylpregna-8,14-dien-3-ol. M.p. 149–151° C.

B) (3β,5α,20R)-20-[(3-Fluorophenyl)methoxy]-4,4-dimethylpregna-8,14-dien-3-ol. M.p. 113–115° C.

C) (3β,5α,20R)-20-[(4-Fluorophenyl)methoxy]-4,4-dimethylpregna-8,14-dien-3-ol. M.p.104–106° C.

D) (3β,5α,20R)-20-[(3,4-Difluorophenyl)methoxy]-4,4-dimethylpregna-8,14-dien-3-ol. M.p. 48–50° C.

E) (3β,5α,20R)-4,4-Dimethyl-20-[[2-(trifluoromethyl)phenyl]methoxy]pregna-8,14-dien-3-ol. M.p. 65–67° C. The product contained 20% of (3β,5α,20R)-4,4-dimethyl-20-[[2-(trifluoromethyl)phenyl]methoxy]pregna-6,8(14)-dien-3-ol.

EXAMPLE 4

(3β,5α,20S)-4,4,20-Trimethyl-21-phenoxypregna-8, 14-dien-3-ol i)—A solution of (20S)-3-oxopregn-4-ene-20-carboxaldehyde (125 g) in dry ethanol (1250 ml) was cooled to −10° C., whereupon a solution of sodium borohydride (4.4 g) in dry ethanol (80 ml) was added in 30 min. After stirring the mixture for 2 hours at −10° C., the reaction was quenched by adding a 50% aqueous solution of acetic acid. The reaction mixture was concentrated under reduced pressure to 25% of its original volume and then poured into ice-water (5 l). The resulting suspension was stirred overnight and filtered. The residue was washed with water and dried to give (20S)-21-hydroxy-20-methylpregn-4-en-3-one (124 g) which was used in the following step without further purification.

ii)—A solution of the alcohol (124 g) obtained in the previous step and of imidazole (176 g) in dry N,N-dimethylformamide (1730 ml) was cooled to 10° C. t-Butyldimethylsilyl chloride (112 g) was added in one portion and the mixture was stirred at room temperature for 2 h. Then it was poured into a mixture of ice-water (10 l) and of a saturated aqueous solution of sodium hydrogen carbonate (750 ml). The resulting suspension was filtered and the residue was washed with water. Drying of the residue afforded (20S)-21-[[(1,1-dimethylethyl)dimethylsilyl]oxy]-20-methylpregn-4-en-3-one (169.3 g), which was used in the following step without further purification.

iii)—A mixture of potassium t-butoxide (169.5 g) and dry t-butanol (3750 ml) was warmed to 45° C. A solution of the ketone obtained in the previous step (169.3 g) in dry tetrahydrofuran (375 ml) was added and the mixture was stirred for 10 min. Iodomethane (187.5 ml) was added in 10 min. and stirrring was continued for 3 h. The reaction mixture was concentrated under reduced pressure to a volume of 1.5 l and then poured into ice-water (10 l). After stirring of the mixture for 2 hours the suspension was filtered. The residue was washed with water, dried and purified by crystallization from acetone to give (20S)-21-[[(1,1-dimethylethyl)dimethylsilyl]oxy]-4,4,20-trimethylpregn-5-en-3-one (136.9 g).

iv)—A solution of the ketone (140 g) obtained in the previous step in dry tetrahydrofuran (1400 ml) was added in 30 min. to an ice-cooled suspension of lithium aluminium hydride (35 g) in tetrahydrofuran (1750 ml). After stirring of the mixture for 1 hour at room temperature, the reaction was quenched by addition of a saturated aqueous solution of sodium sulfate (152 ml), followed by water (39 ml). Ethyl acetate (1750 ml) was added, and the mixture was filtered over celite. The filtrate was concentrated under reduced pressure to give (3β,20S)-21-[[(1,1-dimethylethyl)dimethylsilyl]oxy]-4,4,20-trimethylpregn-5-en-3-ol (136.3 g), which was used in the following step without further purification.

v)—A solution of the alcohol (132.5 g) obtained in the previous step in dry pyridine (1310 ml) was cooled to 0° C. Benzoyl chloride (65.7 ml) was added in 5 min. and the reaction mixture was stirred for 1 h at room temperature. Then it was poured into ice-water (6650 ml) and the resulting suspension was stirred overnight. The precipitate was collected by filtration and washed with water (40–50° C.). The residue was dried and purified by crystallization from acetone to give (3β,20S)-21-[[(1,1-dimethylethyl)dimethylsilyl]oxy]-4,4,20-trimethylpregn-5-en-3-ol benzoate (113.6 g).

vi)—A mixture of the benzoate (94.0 g) obtained in the previous step, dry toluene (810 ml), dry cyclohexane (810 ml) and N-bromosuccinimide (36.1 g) was heated under reflux for 10 min. The reaction mixture was cooled, another portion of N-bromosuccinimide (36.1 g) was added, and reflux was continued for another 10 min. The reaction mixture was cooled, a saturated aqueous solution of sodium thiosulfate (1620 ml) was added and the resulting mixture was stirred for 30 min. The organic phase and the aqueous phase were separated and the latter extracted two times with toluene. The combined organic phases were dried over sodium sulfate and concentrated under reduced pressure. A solution of the crude product thus obtained in dry toluene (2835 ml) and N,N-diisopropylethylamine (284 ml) was heated under reflux for 1 h. Then it was cooled and washed with a saturated aqueous solution of sodium hydrogen carbonate, a saturated aqueous solution of ammonium chloride and with brine, the aqueous phase each time being extracted with ethyl acetate. The combined toluene and ethyl acetate solutions were dried over sodium sulfate and concentrated under reduced pressure to give (3β,20S)-21-[[(1,1-dimethylethyl)dimethylsilyl]oxy]-4,4,20-trimethylpregna-5,7-dien-3-ol benzoate (134 g) which was used in the following step without further purification.

vii)—A mixture of the diene obtained in the previous step (30.9 g), chloroform (300 ml), and a solution of HCl in acetic acid (1 M, 300 ml) was stirred for 45 min. at room temperature and then heated under reflux for another 45 min. After cooling, the mixture was poured into water and the product extracted into dichloromethane. The combined organic phases were washed with water, a saturated aqueous solution of sodium hydrogen carbonate and brine, dried over sodium sulfate and concentrated under reduced pressure. Column chromatography afforded a 5:1 mixture (10.2 g) of (3β,5α,20S)-4,4,20-trimethylpregna-8,14-diene-3,21-diol 21-acetate 3-benzoate and (3β,5α,20S)-4,4,20-trimethylpregna-6,8(14)-diene-3,21-diol 21-acetate 3-benzoate. The mixture was used as such in the next step.

viii)—Following a procedure analogous to that described for step vi of Example 1, the products of the previous step (10.2 g) were converted to the 21-hydroxy derivatives. Column chromatography afforded a 5:1 mixture (8.23 g) of (3β,5α,20S)-4,4,20-trimethylpregna-8,14-diene-3,21-diol 3-benzoate and (3β,5α,20S)-4,4,20-trimethylpregna-6,8(14)-diene-3,21-diol 3-benzoate which was used as such in the following step.

ix)—Following a procedure analogous to that described for step xiii of Example 1, the products of the previous step (3.07 g) were converted to the phenoxy compounds. Column chromatography afforded a 5:1 mixture (3.94 g) of (3β,5α,20S)-4,4,20-trimethyl-21-phenoxypregna-8,14-dien-3-ol benzoate and (3β,5α,20S)-4,4,20-trimethyl-21-phenoxypregna-6,8(14)-dien-3-ol benzoate which was used as such in the following step.

x)—Following a procedure analogous to that described for step ix of Example 1, the products of the previous step (3.94 g) were converted to the 3-hydroxy compounds. Column chromatography afforded a 5:1 mixture (1.79 g) of (3β,5α,20S)-4,4,20-trimethyl-21-phenoxypregna-8,14-dien-3-ol and (3β,5α,20S)-4,4,20-trimethyl-21-phenoxypregna-6,8(14)-dien-3-ol which could be separated from each other by preparative HPLC (column: Waters Symmetry $C_{18}$, 19×150 mm; eluent: acetonitrile/water 4:1). (3β,5α,20S)-4,4,20-Trimethyl-21-phenoxypregna-8,14-dien-3-ol. M.p. 134–137° C.

EXAMPLE 5

Starting from the mixture of (3β,5α,20S)-4,4,20-trimethylpregna-8,14-diene-3,21-diol 3-benzoate and (3β,5α,20S)-4,4,20-trimethylpregna-6,8(14)-diene-3,21-diol 3-benzoate, described under viii of Example 4, and using reaction steps analogous to those described under ix and x of Example 4, the following compounds were prepared:
A) (3β,5α,20S)-4,4,20-Trimethyl-21-(2-methylphenoxy) pregna-8,14-dien-3-ol. M.p. 126–141° C.; $[\alpha]_D^{20}$=−50° (c=0.5, dioxane). The product contained 15% of (3β,5α,20S)-4,4,20-trimethyl-21-(2-methylphenoxy)pregna-6,8(14)-dien-3-ol.
B) (3β,5α,20S)-4,4,20-Trimethyl-21-(4-methylphenoxy) pregna-8,14-dien-3-ol. M.p. 118–124° C.; $[\alpha]_D^{20}$=−49.6° (c=0.5, dioxane). The product contained 15% of (3β,5α,20S)-4,4,20-trimethyl-21-(4-methylphenoxy)pregna-6,8(14)-dien-3-ol.

EXAMPLE 6

(3β,5α,20S)-4,4,20-Trimethyl-21-(phenylthio) pregna-8,14-dien-3-ol i)—Following procedures analogous to those described under i–iv of Example 2, (3β,5α,20S)-4,4,20-trimethylpregna-8,14-diene-3,21-diol 3-benzoate (Example 4, step viii) was converted to (3β,5α,20S)-3-[(1-ethoxyethyl)oxy]-4,4,20-trimethyl-pregna-8,14-dien-21-ol.

ii)—p-Toluenesulfonic anhydride (4.56 g) was added to a solution of (3β,5α,20S)-3-[(1-ethoxyethyl)oxy]-4,4,20-trimethylpregna-8,14-dien-21-ol (3.0 g) in dry pyridine (28 ml). The reaction mixture was stirred at room temperature for 2 h and then poured into water. The product was extracted into ethyl acetate; the combined organic phases were washed with brine, dried over sodium sulfate and concentrated, to give (3β,5α,20S)-3-[(1-ethoxyethyl)oxy]-4,4,20-trimethyl-21-[[(4-methylphenyl)sulfonyl]oxy]pregna-8,14-diene (4.32 g), which was used in the following step without further purification.

iii)—Sodium hydride (0.302 g) was added to a solution of the tosylate described in the previous step (4.03 g) in dry dimethylformamide (40 ml). Thiophenol (0.81 ml) was added and the reaction mixture was stirred for 30 min. at room temperature. The mixture was poured into water and the product was extracted into ethyl acetate. The combined organic phases were washed with brine, dried over sodium sulfate and concentrated. Column chromatography afforded (3β,5α,20S)-3-[(1-ethoxyethyl)oxy]-4,4,20-trimethyl-21-(phenylthio)pregna-8,14-diene (3.0 g).

iv)—Following a procedure analogous to that described under iv of Example 1, the thioether described in the previous step (1.0 g) was converted into (3β,5α,20S)-4,4,20-trimethyl-21-(phenylthio)pregna-8,14-dien-3-ol (0.24 g). M.p. 101–107° C. The product contained 25% of (3β,5α,20S)-4,4,20-trimethyl-21-(phenylthio)pregna-6,8(14)-dien-3-ol.

EXAMPLE 7

[3β,5α,20S,(21R)]-4,4,20-Trimethyl-21-(phenylsulfinyl)pregna-8,14-dien-3-ol and [3β,5α,20S,(21S)]-4,4,20-trimethyl-21-(phenylsulfinyl) pregna-8,14-dien-3-ol i)—Following a procedure analogous to that described under ii of Example 6, (3β,5α,20S)-4,4,20-trimethylpregna-8,14-diene-3,21-diol 3-benzoate (Example 4, step viii, 2.0 g) was converted to (3β,5α,20S)-4,4,20-trimethyl-21-[[(4-methylphenyl)sulfonyl]oxy]pregna-8,14-dien-3-ol benzoate (2.95 g).

ii)—Following a procedure analogous to that described under iii of Example 6, the tosylate obtained in the previous step (2.95 g) was converted to (3β,5α,20S)-4,4,20-trimethyl-21-(phenylthio)pregna-8,14-dien-3-ol benzoate (1.72 g).

iii)—Hydrogen peroxide (30%, 0.6 ml) was added to a solution of the thioether described in the previous step (1.67 g) in dichloromethane (15 ml), followed by trifluoroacetone (0.054 ml). The mixture was stirred at room temperature for 6 h and then poured into a saturated aqueous solution of sodium thiosulfate. The product was extracted into dichloromethane; the combined organic phases were washed with water, dried over sodium sulfate and concentrated, to give a mixture of [3β,5α,20S,(21R)]-4,4,20-trimethyl-21-(phenylsulfinyl)pregna-8,14-dien-3-ol benzoate and [3β,5α,20S,(21S)]-4,4,20-trimethyl-21-(phenylsulfinyl)pregna-8,14-dien-3-ol benzoate (1.73 g), which was used in the following step without further purification.

iv)—Potassium hydroxide (0.464 g) was added to a solution of the mixture of sulfoxides obtained in the previous step (1.73 g) in a mixture of tetrahydrofuran (10.7 ml) and methanol (1.25 ml). The reaction mixture was stirred at room temperature for 2 h and then poured into water. The product was extracted into ethyl acetate; the combined organic phases were washed with water and brine, dried over sodium sulfate and concentrated. Column chromatography of the crude product and crystallization afforded [3β,5α,20S,(21R)]-4,4,20-trimethyl-21-(phenylsulfinyl)pregna-8,14-dien-3-ol (0.16 g), m.p. 185–191° C., containing 20% of [3β,5α,20S,(21R)]-4,4,20-trimethyl-21-(phenylsulfinyl)pregna-6,8(14)-dien-3-ol, and [3β,5α,20S,(21S)]-4,4,20-trimethyl-21-(phenylsulfinyl)pregna-8,14-dien-3-ol (0.306 g), m.p. 187–201° C.

EXAMPLE 8

(3β,5α,20S)-4,4,20-Trimethyl-21-(phenylsulfonyl) pregna-8,14-dien-3-ol i)—Iodine (1.87 g) was added to a mixture of triphenylphosphine (2.04 g), imidazole (0.53 g) and dry dichloromethane (48 ml). After 10 min. stirring (3β,5α,20S)-4,4,20-trimethylpregna-8,14-diene-3,21-diol 3-benzoate (Example 4, step viii, 2.0 g) in dry dichloromethane (20 ml) was added and stirring was continued for 1 h. The reaction mixture was poured into a saturated aqueous solution of sodium thiosulfate and the product was extracted into dichloromethane. The combined organic phases were washed with brine, dried over sodium sulfate and concentrated. Column chromatography afforded (3β,5α,20S)-21-iodo-4,4,20-trimethylpregna-8,14-dien-3-ol benzoate (2.29 g).

ii)—Sodium benzenesulfinate (0.74 g) was added to a solution of the iodide obtained in the previous step (1.72 g) in dry dimethylformamide (7.5 ml). The reaction mixture was stirred at 74° C. for 3 h, cooled, and poured into water. The product was extracted into ethyl acetate; the combined organic phases were washed with brine, dried over sodium sulfate and concentrated. Column chromatography gave (3β,5α,20S)-4,4,20-trimethyl-21-(phenylsulfonyl)pregna-8,14-dien-3-ol benzoate (0.599 g).

iii)—Following a procedure analogous to that described under step iv of Example 7, the sulfone obtained in the previous step (0.809 g) was converted to (3β,5α,20S)-4,4,20-trimethyl-21-(phenylsulfonyl)pregna-8,14-dien-3-ol (0.399 g). M.p. 175–188° C. The product contained 25% of (3β,5α,20S)-4,4,20-trimethyl-21-(phenylsulfonyl) pregna-6,8(14)-dien-3-ol.

EXAMPLE 9

The Oocyte Assay

General

Oocytes arrested in meiosis contain diffused chromosomes which are surrounded by an intact nuclear envelope known as the germinal vesicle (GV). Upon reinitiation of meiosis by the midcycle gonadotropin surge, the chromosomes recondense and the GV breaks down (GVBD). In vivo, the oocyte is exposed to hypoxanthine (HX), which maintains the oocyte arrested in the meiotic prophase. This meiotic arrest can be mimicked in vitro by addition of hypoxanthine to the culture medium. The agonistic activity of the compounds of the invention is measured as the ability to overcome the hypoxanthine maintained meiotic arrest in denuded oocytes (DO) or cumulus enclosed oocytes (CEO), i.e. as the ability to induce meiotic resumption in vitro.

Therefore, natural resumption of meiosis can be mimicked in vitro by addition of FF-Mas or other agonists to the culture medium containing hypoxanthine. The antagonistic activity of the compounds is measured as the ability to inhibit the FF-Mas or 22S-hydroxy-FF-Mas induced oocyte maturation in denuded oocytes or cumulus enclosed oocytes, respectively, in vitro.

Isolation of Cumulus Enclosed Oocytes

Ovaries are obtained from immature female mice (B6D2-F1, strain C57BLxDBA). At the age of 19, 20 or 21 days the mice are injected subcutaneously with a single dose of 20 IU follicle stimulating hormone (Humegon, Organon, The Netherlands) in saline.

Forty-eight hours after follicle stimulating hormone injection mice are killed by cervical dislocation. The ovaries are removed, freed of extraneous tissue and placed in a multi-dish containing 0.5 ml preparation medium at 37° C. L-15 Leibovitz medium (Gibco, pH 7.3±0.1) supplemented with bovine serum albumin (3 mg.ml$^{-1}$), L-glutamine (0.23 mM), sodium pyruvate (2 mM) and hypoxanthine (4 mM) is used as preparation medium. The antral follicles of the ovaries are punctured under a dissecting microscope using two 27-gauge needles attached to two 1 ml syringes. Cumulus enclosed oocytes (CEO) of uniform size are selected with a mouth-controlled pipette and rinsed in 0,5 ml fresh preparation medium. About 20 CEO are obtained from one ovary.

Isolation of Denuded Oocytes

Oocytes freed from cumulus cells, i.e. denuded oocytes (DO), are obtained by gently flushing CEO through a fine-bore mouth-controlled pipette. DO were collected in fresh MEM alpha medium, containing bovine serum albumin (3 mg.ml$^{-1}$), L-glutamine (0.23 mM), sodium pyruvate (2 mM) and hypoxanthine (4 mM), and washed twice before transfer to the test medium.

Experimental Design

The oocyte assay is performed in 3 blocks, each block represents the ovaries of one mouse (randomized block design). At t=0 DO or CEO of the first ovary of the first mouse, are spread over well 1 and 3 and oocytes of the second ovary over well 2 and 4 of a 4-well multidish containing 0.5 ml of culture medium to which a 17β-aryl (arylmethyl)oxy(thio)alkyl-androstane derivative of the invention is added in case of agonistic testing. In case of antagonistic testing, a 17β-aryl(arylmethyl)oxy(thio)alkyl-androstane derivative of the invention is added together with FF-Mas (DO assay) or 22S-hydroxy-FF-Mas (CEO assay) [first block]. In case of agonistic testing, culture medium was used as control; in case of antagonistic testing, culture medium containing FF-Mas (DO assay) or 22S-hydroxy-FF-Mas (CEO assay) was used as control. The same procedure is performed for the second and third mouse [block 2 and 3]. The culture medium used is MEM alpha medium (Gibco, pH 7.3±0.1) saturated with $CO_2$ and supplemented with bovine serum albumin (3 mg.ml$^{-1}$), L-glutamine (0.23 mM), sodium pyruvate (2 mM) and hypoxanthine (4 mM). In total, each control or test compound is tested on 30 oocytes (10 oocytes per block). At t=0 the number of oocytes with intact germinal vesicles (GV) or germinal vesicle break-down (GVBD) is counted under an inverted microscope with differential interference contrast equipment. Only oocytes with an intact GV are used in the experiment. Oocytes are cultured 22 hours at 37° C. in 100% humidified atmosphere with 5% $CO_2$ in air. At the end of the culture period the number of oocytes with GV or GVBD per group is counted. For statistical analysis the percentage germinal vesicle breakdown is calculated for each group in one block. These percentages are subjected to arcsin transformation, and differences between control and test compounds are analyzed by an ANOVA test for a randomized block design. Results are presented in Table I (agonists) and II (antagonists).

TABLE I

Percentage germinal vesicle breakdown (GVBD) in oocytes following culturing in the presence of test compounds in agonistic testing.

| Compound* | % GVBD DO assay exp.(control) | CEO assay exp.(control) |
|---|---|---|
| (3β,5α,20R)-4,4-dimethyl-20-phenoxypregna-8,14-dien-3-ol (Example 1) | 100(0) | 96(0) |
| (3β,5α,20R)-4,4-dimethyl-20-(phenylmethoxy)-pregna-8,14-dien-3-ol (Example 2) | 100(11) | 59(0) |
| (3β,5α,20S)-4,4,20-trimethyl-21-phenoxy-pregna-8,14-dien-3-ol (Example 4) | 72(3) | 1(0) |
| (3β,5α,20S)-4,4,20-trimethyl-21-(2-methyl-phenoxy)pregna-8,14-dien-3-ol (Example 5A) | 100(6) | 7(0) |
| (3β,5α,20S)-4,4,20-trimethyl-21-(4-methyl-phenoxy)pregna-8,14-dien-3-ol (Example 5B) | 87(3) | 16(4) |
| (3β,5α,20R)-4,4-dimethylcholesta-8,14,24-trien-3-ol (FF-Mas) | 84(7) | 0(0) |
| (3β,5α,20S,22S)-4,4-dimethylcholesta-8,14, 24-triene-3,22-diol (22S-hydroxy-FF-Mas)** | 97(2) | 73(2) |

*Each compound was tested at a concentration of 10 μM.
**Tested at a concentration of 5 μM.

TABLE II

Percentage germinal vesicle breakdown (GVBD) in oocytes following culturing in the presence of test compounds and FF-Mas (DO assay) or 22S-hydroxy-FF-Mas (CEO assay) in antagonistic testing.

| Compound | % GVBD DO assay* exp.(control) | CEO assay** exp.(control) |
|---|---|---|
| (3β,5α,20S)-4,4,20-trimethyl-21-(phenyl-thio)pregna-8,14-dien-3-ol (Example 6) | 64(94) | |
| (3β,5α,20S)-4,4,20-trimethyl-21-(phenyl-sulfonyl)pregna-8,14-dien-3-ol (Example 8) | 32(84) | 14(89) |

*Concentration of (3β,5α,20R)-4,4-dimethylcholesta-8,14,24-trien-3-ol (FF-Mas): 5 μM; concentration of compound tested: 5 μM.
**Concentration of (3β,5α,20S,22S)-4,4-dimethylcholesta-8,14,24-triene-3,22-diol (22S-hydroxy-FF-Mas): 5 μM; concentration of compound tested: 2.5 μM.

What is claimed is:

1. A 17β-aryl(arylmethyl)oxy(thio)alkyl-androstane derivative having the general formula [I]

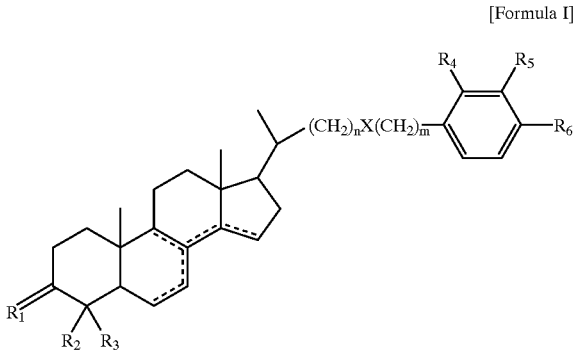

[Formula I]

wherein $R_1$ is (H,OR), (H,OSO$_3$H) or NOR, with R being H, (C$_{1-6}$)alkyl or (C$_{1-6}$)-acyl; each of $R_2$ and $R_3$ is independently hydrogen or (C$_{1-6}$) alkyl; n is 0, 1 or 2; X is O, S, S(O)$_2$; m is 0 or 1; each of $R_4$, $R_5$ and $R_6$ is independently hydrogen, hydroxy, (C$_{1-4}$)alkoxy, halogen, NR$_7$R$_8$ or (C$_{1-4}$) alkyl and each of $R_7$ and $R_8$ is independently hydrogen or (C$_{1-4}$)alkyl; and wherein the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$; or a pharmaceutically acceptable salt thereof.

2. The 17β-aryl(arylmethyl)oxy(thio)alkyl-androstane derivative according to claim 1, wherein n is 0 or 1, X is O, S, S(O) or S(O)$_2$ and m is 0 or 1.

3. The 17β-aryl(arylmethyl)oxy(thio)alkyl-androstane derivative according to claim 2, wherein $R_1$ is (H,OR), and R is H or (C$_{1-6}$)acyl, the dotted lines indicate a $\Delta^{8,14}$ diene system, and the configuration of the 3-OR substituent is the β-configuration.

4. A 17β-aryl(arylmethyl)oxy(thio)alkyl-androstane derivative selected from the group consisting of (3β,5α,20R)-4,4-dimethyl-20-phenoxypregna-8,14-dien-3-ol, (3β,5α,20R)-4,4-dimethyl-20-(phenylmethoxy)pregna-8,14-dien-3-ol, (3β,5α,20S)-4,4,20-trimethyl-21-(2-methylphenoxy)pregna-8,14-dien-3-ol and (3β,5α,20S)-4,4,20-trimethyl-21-(phenylsulfonyl)pregna-8,14-dien-3-ol.

5. A method for regulating meiosis comprising administering an effective amount of the 17β-aryl(arylmethyl)oxy (thio)alkyl-androstane derivative of claim 1 or a pharmaceutically acceptable salt thereof.

6. A pharmaceutical composition comprising the 17β-aryl (arylmethyl)oxy(thio)alkyl-androstane of claim 1 or a pharmaceutically acceptable salt thereof, in admixture with pharmaceutically acceptable auxiliaries.

7. A method for controlling fertility comprising administering an effective amount of the 17β-aryl(arylmethyl)oxy (thio)alkyl-androstane derivative of claim 1 or a pharmaceutically acceptable salt thereof.

8. The 17β-aryl(arylmethyl)oxy(thio)alkyl-androstane derivative according to claim 1, wherein each of the $R_4$, $R_5$ and $R_6$ is independently substituted by hydrogen, alkoxy, halogen or oxo.

* * * * *